(12) United States Patent
Bather et al.

(10) Patent No.: US 8,604,422 B2
(45) Date of Patent: Dec. 10, 2013

(54) IDENTIFICATION OF ANALYTES BY AN ION MOBILITY SPECTROMETER WITH FORMATION OF DIMER ANALYTES

(71) Applicants: Wolfgang Bather, Lubeck (DE); Frank Gunzer, Kronshagen (DE)

(72) Inventors: Wolfgang Bather, Lubeck (DE); Frank Gunzer, Kronshagen (DE)

(73) Assignee: Dragerwork AG & Co. KGaA, Lubeck (DE)

( * ) Notice: Subject to any disclaimer, the term of this patent is extended or adjusted under 35 U.S.C. 154(b) by 0 days.

(21) Appl. No.: 13/720,259

(22) Filed: Dec. 19, 2012

(65) Prior Publication Data

US 2013/0200259 A1    Aug. 8, 2013

(30) Foreign Application Priority Data

Dec. 20, 2011  (DE) .......................... 10 2011 121 669

(51) Int. Cl.
*H01J 49/00*    (2006.01)
(52) U.S. Cl.
CPC ...................................... *H01J 49/00* (2013.01)
USPC ......................................................... 250/286
(58) Field of Classification Search
USPC ................................................. 250/286, 282
See application file for complete search history.

(56) References Cited

U.S. PATENT DOCUMENTS

| 5,234,838 | A | 8/1993 | Bacon, Jr. | |
| 7,078,679 | B2 * | 7/2006 | Westphall et al. | 250/287 |
| 2012/0032073 | A1 * | 2/2012 | Rand et al. | 250/282 |

FOREIGN PATENT DOCUMENTS

| DE | 10 2006 019 463 A1 | 11/2007 |
| DE | 10 2008 029 555 1 | 1/2010 |
| EP | 0 135 747 A2 | 4/1985 |
| GB | 2474924 A | 5/2011 |
| WO | WO 2006/129101 A1 | 12/2006 |

OTHER PUBLICATIONS

Frank Gunzer et al., "A novel non-radioactive electron source for ion mobility spectrometry," Int. Journal for Ion Mobil. Spec., vol. 13 (2010), Issue 1, pp. 9-16.
Wolfgang Baether et al., "Investigation of the influence of voltage parameters on decay times in an ion mobility spectrometer with a pulsed non-radioactive electron source," Int. Journal for Ion Mobil. Spec., vol. 13 (2010), Issue 3-4, pp. 95-101.
Andre Heptner et al., "Investigation of ion-ion-recombination at atmospheric pressure with a pulsed electron gun," Analyst, vol. 137 (1012), pp. 5105-5112.
Wolfgang Baether et al., "Pulsed Ion Mobility Spectrometer for the Detection of Toluene 2,4-Diisocyanate in Ambient Air," IEEE Sensors Journal, vol. 12, No. 6 (2012), pp. 1748-1754.
Wolfgang Baether et al., "Quantitative information in decay curves obtained with a pulsed ion mobility spectrometer," Analyst (2012), vol. 137, pp. 2723-2727.
Fran Gunzer et al., "Application of a Nonradioactive Pulsed Electron Source for Ion Mobility Spectrometry," Anal. Chem. (2010), 82, pp. 3756-3763.

(Continued)

*Primary Examiner* — Kiet T Nguyen
(74) *Attorney, Agent, or Firm* — Locke Lord LLP; Peter J. Fallon; Alan B. Clement

(57) ABSTRACT

The subject of the invention is a method for identification of analytes with an ion mobility spectrometer by performing a series of measurements while varying the residence time of the analytes in the reaction space and identifying of monomer and nascent dimer analytes in the spectra so obtained.

23 Claims, 5 Drawing Sheets

(56) References Cited

OTHER PUBLICATIONS

Figure 1:
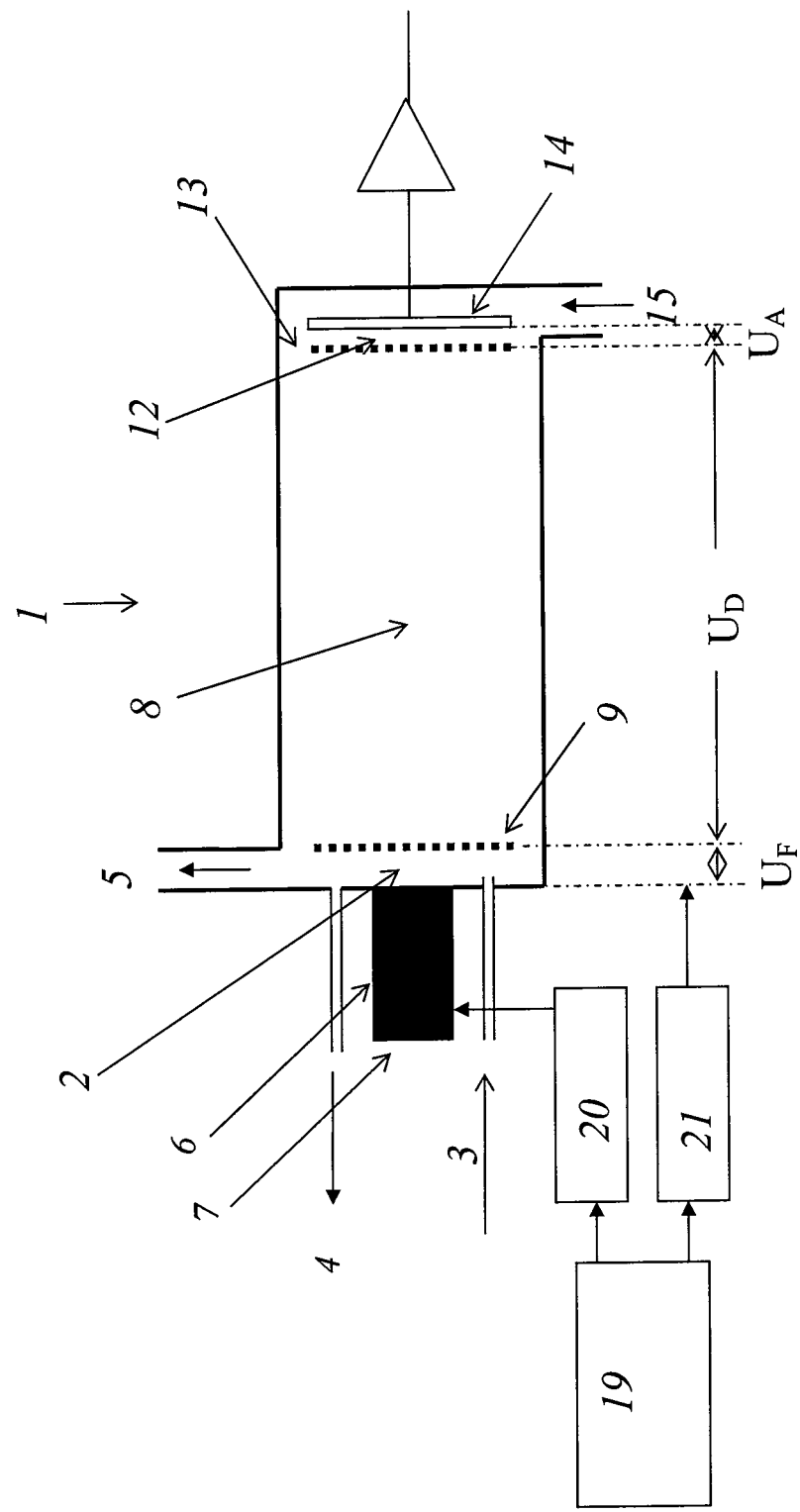

Wolfgang Baether et al., "Pulsed electron beams in ion mobility spectrometry," Reviews in Anal. Chem. (2012), vol. 31 (3-4), pp. 139-152.

Wolfgang Baether et al., "Signal decay curves obtained with a pulsed electron gun allow for improved analyte identification power of ion mobility spectrometers by distinction of monomer and dimer signals," Elsevier, Sensors and Actuators B: Chemical (2012), vol. B171-172, pp. 1238-1243.

Philipp Cochems et al., "Selective ion suppression as a pre-separation method in ion mobility spectrometry using a pulsed electron gun," Int. J. Ion Mobil. Spec. (2012), vol. 15(1), pp. 31-39.

Frank Gunzer et al., "Investigation of dimethyl methylphosphonate (DMMP) with an Ion mobility spectrometer using a pulsed electron source," Int. J. Ion Mobil. Spec. (2011), vol. 14(2-3), pp. 99-107.

* cited by examiner

IDENTIFICATION OF ANALYTES BY AN ION MOBILITY SPECTROMETER WITH FORMATION OF DIMER ANALYTES

The present application claims priority to German Application No.: DE 10 2011 121 669.7, filed Dec. 20, 2011, and entitled: Indentification Of Analytes By An Ion Mobility Spectrometer With Formation Of Dimer Analytes.

The invention concerns a method for identification of analytes with an ion mobility spectrometer by performing a series of measurements while varying the residence time of the analytes in the reaction space and identifying of monomer and nascent dimer analytes in the spectra so obtained.

PRIOR ART

Ion mobility spectrometers (IMS) are used for determination of very small concentrations of analytes in a gaseous matrix. They are distinguished in particular by high sensitivity, short measurement duration and, for certain substances, a good selectivity. Since the IMS can be small in design, low weight, and with low power consumption, they are also suitable as portable measurement systems. IMS are used in particular for the detection of explosives, chemical warfare agents, drugs and toxic industrial chemicals.

An IMS generally has a reaction space and a drift space. In a further ionization space, according to one possible configuration, there is an electron emitter to produce free electrons. The free electrons are accelerated by means of an electron flux modulator and an acceleration voltage imposed between the electron emitter and the electron flux modulator in the direction of an electron-transparent but gas-tight membrane between the ionization space and the reaction space. The accelerated electrons go through the membrane into the reaction space filled with drift gas and analyte gas. In this partial chamber, the impinging electrons produce charged gas particles. The charging of the gas particles results in the forming of charged analytes. Under the action of a drift voltage, the charged analytes move from the reaction space to a trapping electrode situated in the drift space, where they are detected. Since the different charged analytes have different mobility and therefore different drift velocity, the different analytes take different times to get from the charging zone situated in front of the membrane to the trapping electrode.

The measurement principle of the ion mobility spectrometer is based on the fact that the analyte molecules being determined in a chemical gas-phase reaction with a reactant ion cluster are converted into another ion cluster. Ideally, these newly formed analyte-specific clusters differ in mass, chemical composition, and/or three-dimensional structure.

The product ion mixture formed after a defined time is separated on the basis of the different particular mobility of the ion clusters, e.g., at atmospheric pressure, by means of an electrical field, detected as a function of time, and represented as an ion mobility spectrum. From this, one can determine concentration and analyte species. The time that it takes the ion clusters to get to the detector from the time of transfer from the reaction space to the drift space is a characteristic feature of the particular analyte. The resolution of the IMS in the case of commercial machines is 30 to 50 and for research models it is up to 100 (resolution=drift time/half-width of the corresponding peak).

With a resolution of 50, e.g., one can distinguish two peaks A and B that have drift times of, say, 7.5 ms and 7.65 ms. But now there are a multitude of substances that also have a drift time of, say, 7.65 ms. Hence, an unambiguous identification of a substance is no longer possible. To heighten the potential for identification, the resolution for example can be improved even further. But this requires rather expensive and sophisticated spectrometer layouts.

Another way is the simultaneous recording of negative spectra. But this presupposes that the analyte of interest also puts out a negative spectrum. Furthermore, increased instrument expense is necessary, which requires, say, a second IMS or a rapid pole reversal with relative high voltages (e.g., 2 kV).

STATEMENT OF THE PROBLEM

The problem of this invention is to provide an IMS or a method with better identification potential, especially to accomplish a more unambiguous identification of substances with the same or very similar drift times.

SUMMARY OF THE INVENTION

The present invention is defined by the independent claim. Preferred embodiments are the subject of the subclaims or described hereafter.

The present invention utilizes a spectrometer and a method for spectroscopy with charged analytes, as is described in DE 102008029555 A1 for an ion mobility spectrometer. DE 102008029555 A1 is accordingly also expressly made part of the disclosure of this application. The method comprises the following steps:
  introducing a gas being studied, containing analytes, into a reaction space, carrying out an ionization process in which charged analytes are created in the reaction space by means of an ionizer,
  carrying out a transfer process by which the charged analytes are taken from the reaction space to the drift space, and drifting of the charged analytes in the drift space to a detector by means of a drift field present in the drift space and detecting of the analytes reaching the detector and the drift time of the analytes.

In the reaction space of an ion mobility spectrometer, primary ions (such as nitrogen radical cations) are first formed as a result of the electron pulse, which then go through subsequent reactions with water molecules to form hydronium ions. These form the RIP (reactant ion peak) that is typical of ion mobility spectra. If analyte ions with a proton affinity greater than water are also present in the reaction space, a proton transfer ensues from the hydronium ions to the analyte molecules, forming protonated analyte molecules.

With the transfer process from the reaction space to the drift space, these analyte ions are accelerated toward the detector and detected in the form of an ion mobility spectrum. The residence times in the reaction space (time between the start of the electron or photon pulse and the start of the transfer process to the drift space) amount to as much as 1 ms. The fields referred hereinto are in each case electrostatic fields.

If one increases the residence time of the protonated analyte molecules in the reaction space, the protonated analyte molecules can add a further molecule, preferably analyte molecules or tracer molecules, and form so-called dimers.

The dimer is composed of a proton and, say, two analyte molecules. These dimers only attain significant intensities with rather long residence times in the reaction space, but then they can be identified as analyte-characteristic features and be assigned to the monomer or monomers. Dimers can also be composed of two different analytes or one analyte and one known trace, which is added in order to produce dimers with a longer drift time than the analyte. The tracer preferably has a high proton affinity. Independently thereof the proton affinity of the tracer and that of the analyte preferably differ by no more than 100 kJ/mol, most preferably not more than 50 kJ/mol.

While the monomers decrease in intensity with increasing residence time in the reaction space, the intensity of the dimers increases in a spectrum. In this way, monomer peaks can be clearly distinguished from dimer peaks in an IMS spectrum by taking a series of spectra while varying the residence time in the reaction space. This can be used to identify monomers and dimers, even in a complex IMS spectrum.

By combination of the drift times of monomers and dimers, the identification potential in the IMS spectra is distinctly enhanced. An analyte is then described by the drift times of both the monomer and the dimer or dimers.

DETAILED PRESENTATION OF THE INVENTION

Figure 2:
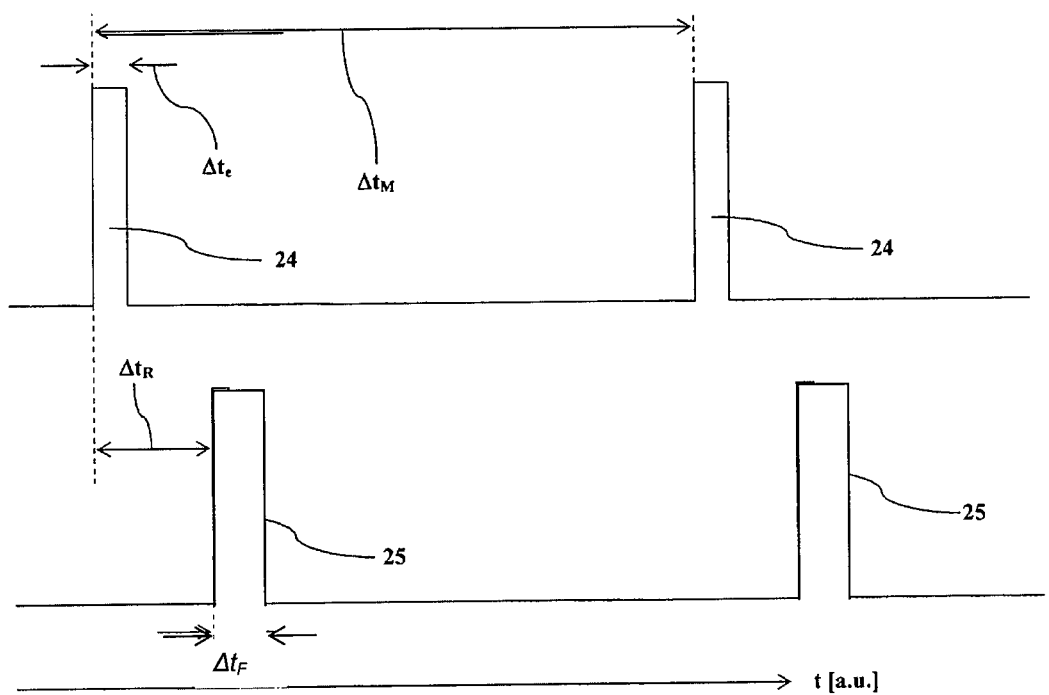
Figure 3:
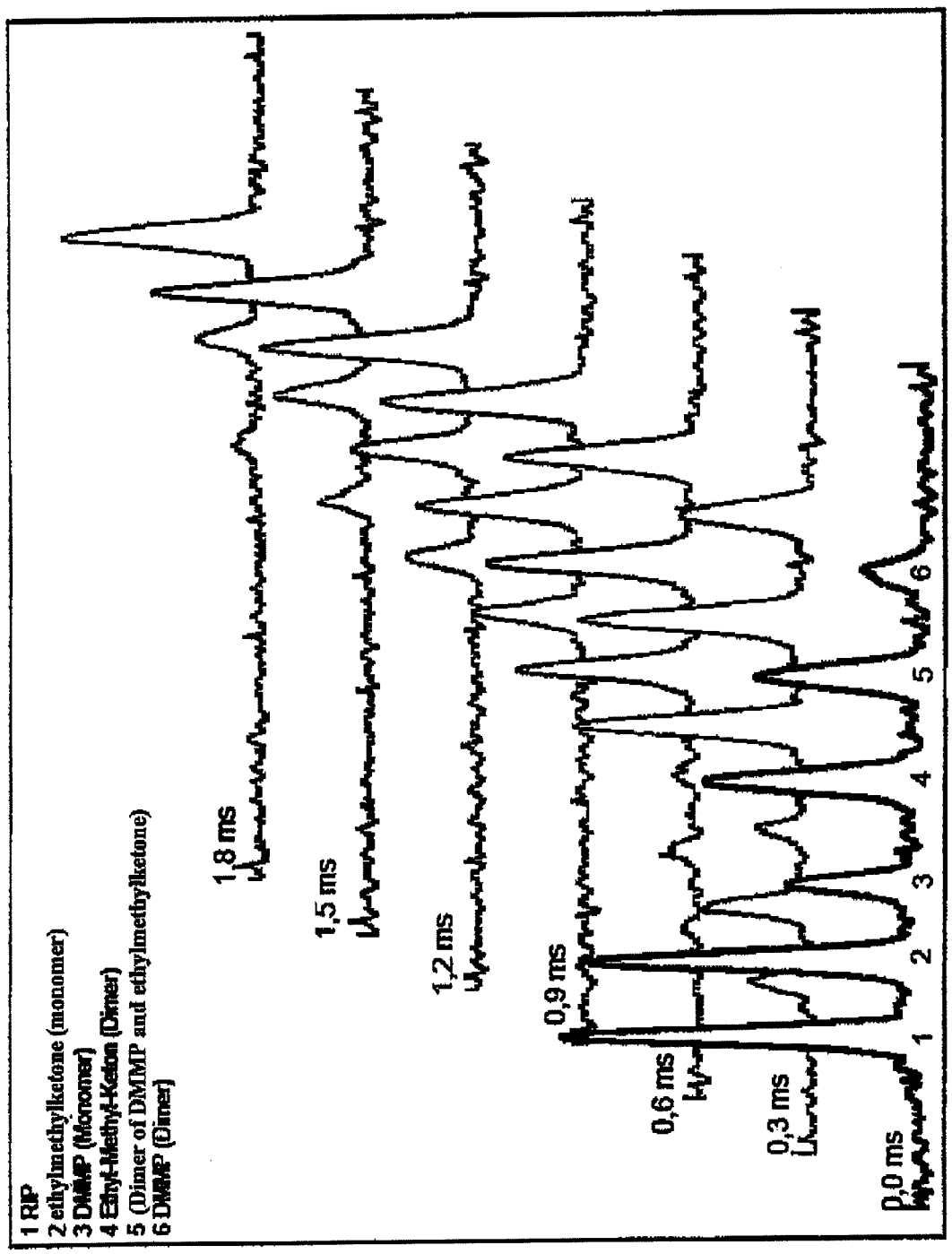
Figure 4:
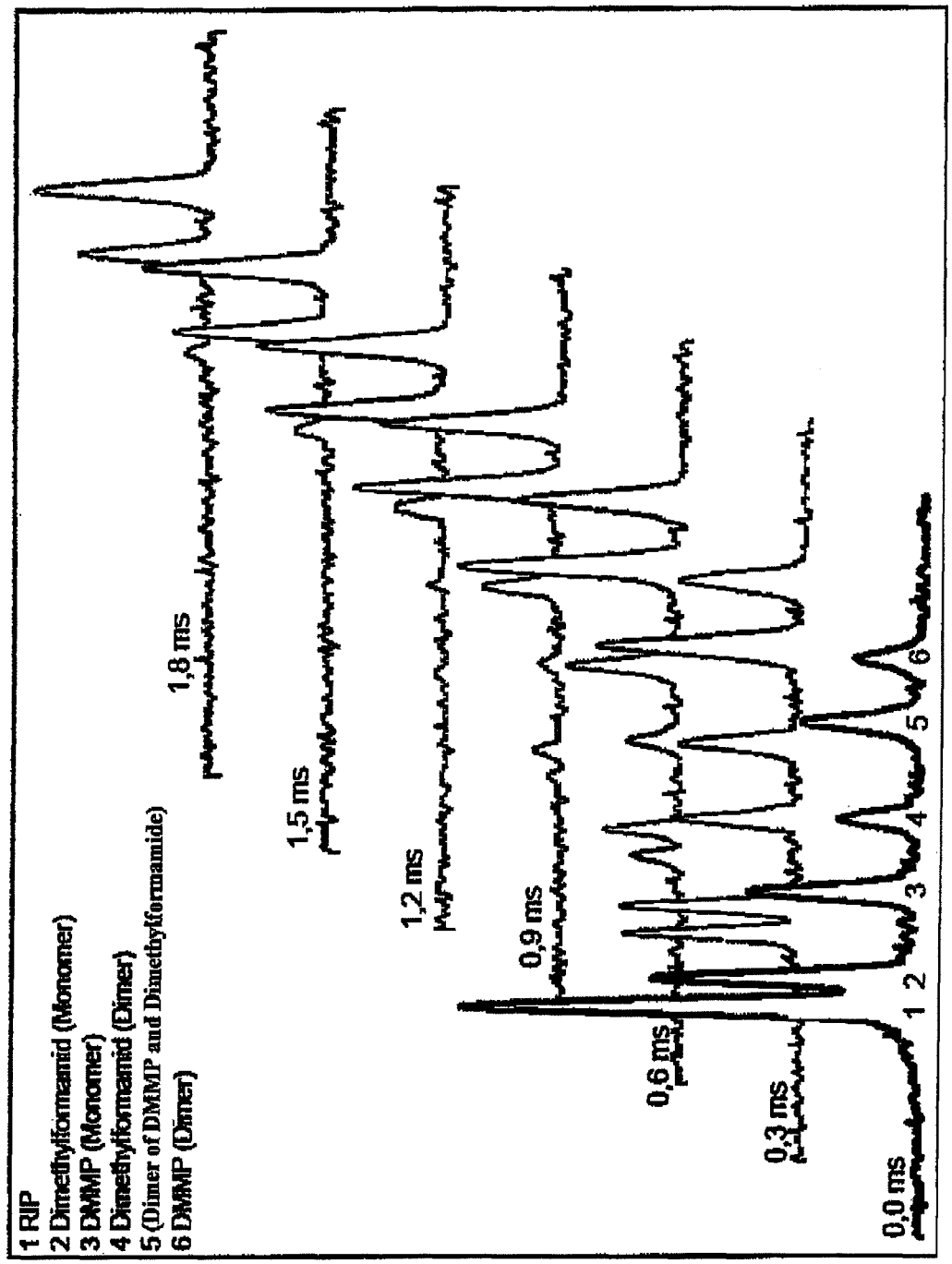
Figure 5:
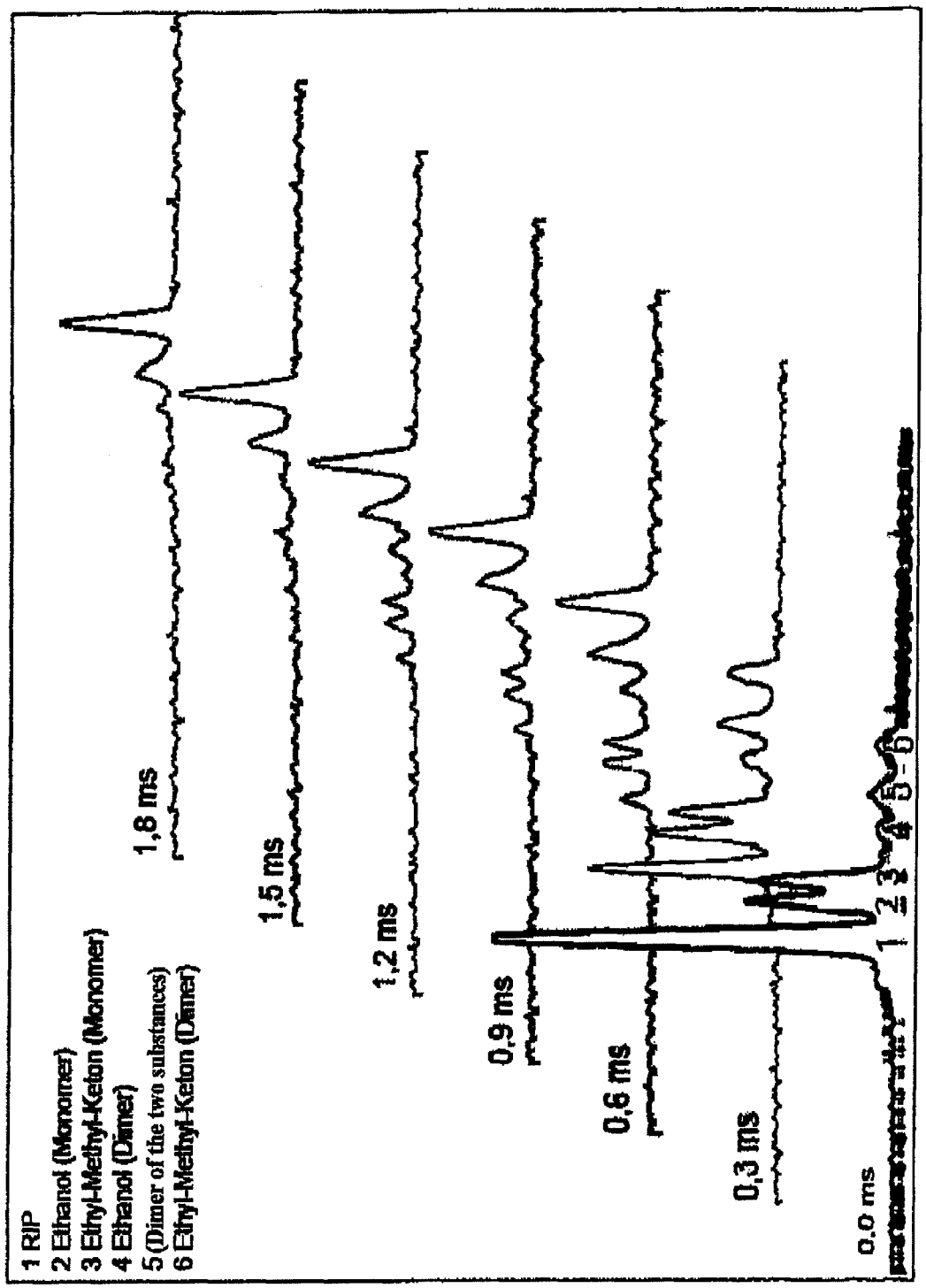

The invention shall be further explained with reference to the following figures and their description, without being limited to these. There are shown:

FIG. 1 the layout of an ion mobility spectrometer,

FIG. 2 the time curve of two measurement sequences with pulsed electron source with ionization pulse I and time-delayed ion extraction pulse F, FIG. 3 Ion mobility spectra of a mixture of ethylmethylketone and dimethylmethylphosphonate (DMMP) as a function of the residence time $\Delta t_R$ in the reaction space, FIG. 4 Ion mobility spectra of a mixture of dimethylformamide and DMMP as a function of the residence time $\Delta t_R$ in the reaction space, and FIG. 5 Ion mobility spectra of a mixture of ethanol and ethylmethylketone as a function of the residence time $\Delta t_R$ in the reaction space FIG. 1 shows an IMS 1 that serves to determine charged analytes in a sample gas being studied and which can be used to identify the species of the charged analytes and determine their concentration. For this, the charged analytes are selected in terms of their drift behavior and also in terms of their recombination behavior subsequent to their generation process.

The IMS 1 has a reaction space 2, which is provided with an inlet 3 and an outlet 4 for the sample gas being studied. The IMS 1, moreover, has an ionizer 6, which is provided with a pulsed electron source 7 arranged on an outer wall between the inlet 3 and the outlet 4 for the sample gas, which emits ionization pulses I with a pulse width $\Delta t_e$ at the interval of a time $\Delta t_M$. Alternatively, the ionizer 6 can be or contain a photon source to accomplish a photoionization of the sample gas being studied. The photon source emits photon pulses which ionize the sample gas being studied.

Between the reaction space 2 and a drift space 8 is arranged a pulser grid 9. The pulser grid 9 is connected to a pulse source 21, which enables a pulsed opening and closing of the pulser grid 9 by means of an ion extraction pulse F that is delayed in time relative to the ionization pulse I. The ion extraction pulse F can be triggered, e.g., in the form of a transfer voltage $U_F$ of 100 to 300 V. An $U_F$ of 200 V results, e.g., from a drift voltage of 2000 V and an ion extraction voltage of 2200 V.

In an end zone of the drift space 8 opposite the pulser grid 9 there is provided a detector space 12, which consists of an aperture grid 13 and a Faraday receiver 14. Between the pulser grid 9 and the aperture grid 13 there can be imposed a drift voltage $U_D$ on the order of, e.g., 200 to 400 Volt/cm of drift length, which creates a homogeneous d.c. field, the so-called drift field, between the two components. A drift voltage of 1000 to 3000 V is customary.

Furthermore, the drift space 8 has at the end zone an inlet 15 for the gaseous drift medium, generally dry air, flowing through the drift space 8 from the detector space 12 to the pulser grid 9. The drift medium can be provided with a tracer in order to form certain dimers.

The detector space 12 is moreover connected to a signal processing unit, which is coupled to a control unit. The control unit consists, e.g., of a computer with a monitor and a keyboard and it controls the drift voltage Up that can be imposed between the pulser grid and the detector space.

Thanks to the aperture grid resistance, a potential $U_D$ is built up across the detector space 12, whose electric field has a focusing influence on the ion peaks.

The control unit is furthermore connected to another control unit, which is formed from a delay generator 19, a first pulse unit 20 and a second pulse unit 21.

Thanks to the control unit, the delay generator 19, an ionization signal can be applied to the ionizer 6 in that the first pulse unit 20 applies a signal to the electron source 7 so that the pulsed electron source 7 puts out an ionization signal and accomplishes an ionization process for the sample gas being studied. The pulse width of the ionization signal corresponds to the pulse width $\Delta t_e$ of the electron pulse or the photon pulse, so that a direct time coordination exists between the ionization signal and the ionization pulse I bringing about the ionization.

Moreover, the blocking device can be subjected to an ion extraction pulse F generated by the control unit in that the second pulse unit 21 sends a corresponding pulselike signal, the ion extraction pulse F, of length $\Delta t_F$, to the pulse source 21 coordinated with the pulser grid 9. The pulse width $\Delta t_F$ corresponds to the pulse width of the ion extraction pulse F. The ion extraction pulse F sent to the blocking device causes the imposing of an extraction field with an electrical field strength on the order of, say, 1000 V/cm, on the reaction space 2, which accelerates the charged analytes in the direction of the pulser grid 9 and lets them pass through the pulser grid 9 into the drift space 8.

Otherwise, the reaction space 2 is essentially free of fields. In particular, when no extraction field is present in the reaction space 2, a weak field with electric field strengths in the range of 10 V/cm is generated, which prevents the charged analytes from getting by diffusion into the drift space 8 from the reaction space 2.

An extraction field is generated by applying a transfer voltage $U_F$ between the pulser grid 9 and a wall of the drift space 8 or the reaction space 2 that is opposite the pulser grid 9. In order to generate a homogeneous extraction field in the reaction space 2, an entrance membrane of the pulsed electron source 7, through which the electrons get into the reaction space 2, can be metallized on one end facing the reaction space 2.

The delay generator 19 controls a time interval $\Delta t_R$ between the ionization pulse I and the ion extraction pulse F, so that an ion extraction pulse F is put out staggered in time relative to the ionization signal.

During the operation of the ion mobility spectrometer 1, the sample gas being studied is admitted through the inlet 3 into the reaction space 2. The sample gas is ionized during an ionization process by reactant ions, which have been formed by gas-phase reaction of the electron pulses emitted by the pulsed electron source 7 with gas molecules of the drift gas, so that the charged analytes of positive and negative charge are produced. For this, the first pulse unit 20 applies the ionization signal to the pulsed electron source 7. The charged analytes recombine after being formed, depending on their reaction rate constants, with oppositely charged analytes or reactant ions.

During the transfer process of the charged analytes into the drift space 8, staggered in time by $\Delta t_R$, the extraction field in the reaction space 2 is applied to the essentially field-free reaction space 2 and the nascent analytes are separated from each other depending on their charge and accelerated toward the pulser grid 9. This interrupts the recombination of the nascent analytes and transfers the charged analytes as analyte packets of definite spatial and temporal resolution to the drift space 8.

The analytes drift depending on their mobility to the detector space 12, pass through the aperture grid 13 and are detected by the Faraday receiver 14. The detector current measured as a function of the drift time $t_D$, of the detected analytes can be used to determine their species and/or concentration.

FIG. 2 shows schematically two ionization pulses I (24) and two ion extraction pulses F (25) of a measurement sequence. Both of them have a pulselike trend and indicate the time during which the electrons are injected into the reaction space 2, as well as the time during which the ion extraction pulse F acts on the pulser grid 9 and the latter is "opened". The ionization signal can be imposed from the outside on the electron source 7 or be generated internally in the electron source 7. For example, the ion extraction pulse F can be used to control an acceleration voltage by which the electrons from a heating coil are accelerated in the direction of the membrane 23. The ion extraction pulse F constitutes a control signal that is applied to the pulse source 21 or that is generated internally in the pulse source 21 to control the trend of the transfer voltage $U_F$.

The partial measurement sequence shown in FIG. 2 shows a twofold repetition of similar pulselike ionization pulses I and likewise similar ion extraction pulses F. An ionization pulse I of a measurement cycle has a definite pulse width $\Delta t_e$ and brings about the ionization of the sample gas introduced into the reaction space 2, thus producing the charged analytes. The electrons emitted during the ionization signal react with gas molecules in the reaction space 2, so that reactant ions of positive and negative charge arise. The reactant ions ionize the sample gas. Two consecutive ionization pulses 24 are staggered by a repetition time $\Delta t_M$, which at the same time establishes the measurement frequency of the spectra taken with the detector. The repetition time $\Delta t_M$ corresponds to or better yet exceeds at least one typical drift time for analytes from the pulser grid 9 to the detector space 12, so that a time overlap of two different analyte packets during the same measurement cycle is avoided. At the time interval $\Delta t_R$ from the ionization pulse I, the ion extraction pulse F is generated, bringing about the imposing of the extraction field on the reaction space 2 and the opening of the pulser grid 9 for the duration $\Delta t_F$ of the ion extraction pulse F (25).

Preferably, the pulse width $\Delta t_e$ of the ionization pulse I is shorter than the pulse width $\Delta t_F$ of the ion extraction pulse F, so that the analytes are transferred to the drift space 8 in a narrow time slot. In the time $\Delta t_R$ (retention time) between the start of the ionization pulse I (24) and the start of the ion extraction pulse F (25) the nascent analytes remain in the reaction space 2 and recombine in dependence on their particular reaction rate constants with oppositely charged analytes or reactant ions, so that the concentration of the charged analytes in the reaction space 2 drops off with time.

The pulse width $\Delta t_e$ of the ionization pulse 24 is between 0.1 microseconds and 10 milliseconds, preferably between 1 microsecond and 1 millisecond and even more preferably between 10 microseconds and 0.1 milliseconds. The pulse width $\Delta t_F$ of the ion extraction pulse 25 can preferably be chosen between 0.5 microseconds and 20 milliseconds, more preferably between 5 microseconds and 2 milliseconds and even more preferably between 50 microseconds and 200 microseconds.

The time interval $\Delta t_R$ between an ionization pulse I and a subsequent ion extraction pulse F is preferably between 10 microseconds and 100 milliseconds and more preferably between 100 microseconds and 10 milliseconds, in particular for the second and each further measurement until the last measurement.

The pulse width $\Delta t_e$ of the ionization pulse I and the pulse width $\Delta t_F$ of the ion extraction pulse F are held constant for a measurement series and the time interval $\Delta t_R$ between the ionization pulse I and the ion extraction pulse F are varied for each measurement in a measurement cycle.

EXPERIMENTAL EXAMPLES

Example 1

Measurements were carried out with a spectrometer "Drager Ion Mobility Spectrometer GSM" with a reaction space around 3 mm in length, a drift space around 7 cm in length, and a detector space around 0.5 mm in length. The pulse width of the pulse $\Delta t_e$ was 10 μs for all examples, the pulse width of the ion extraction pulse $\Delta t_F$ was 110 μs for all examples. The residence times $\Delta t_R$ are indicated each time at the left of the graph in FIGS. 3 to 5.

The transfer voltage $U_F$ was 200 V and the $U_D$ drift voltage was 2000 V. The pulsed electron source is described more closely in the article by F. Gunzer, A. Ulrich and W. Baether: "A novel non-radioactive electron source for ion mobility spectrometry", Int. J. Ion Mobil. Spec., vol. 13 (2010), p. 9-16.

FIG. 3 shows IMS spectra of a mixture of ethylmethylketone and dimethylmethylphosphonate (DMMP). Peak 1 corresponds to the RIP, peak 2 to the monomer of ethylmethylketone and peak 3 to the monomer of DMMP. The dimer of ethylmethylketone corresponds to peak 4 and the dimer of DMMP to peak 6. Peak 5 is a dimer of DMMP and ethylmethylketone.

Example 2

FIG. 4 shows IMS spectra of a mixture of dimethylformamide and DMMP. Peak 1 corresponds to the RIP, peak 2 to the monomer of dimethylformamide and peak 3 to the monomer of DMMP. The dimer of dimethylformamide corresponds to peak 4 and the dimer of DMMP to peak 6. Peak 5 is a dimer of DMMP and dimethylformamide.

Example 3

FIG. 5 shows IMS spectra of a mixture of ethanol and ethylmethylketone. Peak 1 corresponds to the RIP, peak 2 to the monomer of ethanol and peak 3 to the monomer of ethylmethylketone. The dimer of ethanol corresponds to peak 4 and the dimer of ethylmethylketone to peak 6. Peak 5 is a dimer of ethanol and ethylmethylketone.

The respective fundamental spectra with short residence time in the reaction space are shown bolded (each time in the foreground). If one increases the residence time of the ions in the reaction space, the monomers recombine or react further to form dimers. As a result, the monomers 2 and 3 each time fall off in intensity rather quickly, but the dimers at first increase in intensity or remain stable much longer than the monomers.

Thus, it is possible to identify and classify monomers and dimers even of unknown analytes in an IMS spectrum.

LIST OF REFERENCE SYMBOLS 1 ion mobility spectrometer
2 reaction space
3 inlet
4 gas outlet
5 drift medium outlet
6 ionizer
7 pulsed electron source
8 drift space
9 pulser grid
12 detector space
13 aperture grid
14 Faraday receiver
15 drift medium inlet
19 delay generator
20 pulse unit
21 pulse unit 2
24 ionization pulse I
25 ion extraction pulse F
$\Delta t_R$ residence time in the reaction space
$\Delta t_e$ pulse width of the ionization pulse
$\Delta t_F$ pulse width of the ion extraction pulse
$\Delta t_M$ time interval between two ionization pulses
$\Delta U_F$ transfer voltage
$\Delta U_A$ potential of the detector space
$U_D$ drift voltage
$t_D$ drift time

The invention claimed is:

1. A method for spectroscopy with charged analytes, comprising at least the following steps:
   introducing a gas sample comprising a gas mixture into a reaction space;
   carrying out an ionization process in the reaction space to create charged analytes by letting an ionization pulse I act for a time interval $\Delta t_e$ on the gas mixture;
   subsequent carrying out of a transfer process by letting an ion extraction pulse F act for a time interval $\Delta t_F$ on the charged analytes in the gas mixture by which the charged analytes are taken by the extraction field produced from the ion extraction pulse F from the reaction space into a drift space;
   drifting of the charged analytes in the drift space to a detector by means of a drift field present in the drift space and obtaining analyte signals from the analytes reaching the detector,
   wherein at least 3 measurements are performed and spectra recorded for one gas comprising analytes, wherein the spectra give the intensity of the analyte signals versus the drift time and for measurement to measurement the residence time in the reaction space $\Delta t_{Rn}$ is changed between the start of the ionization pulse I and the start of the ion extraction pulse F,
   wherein the peaks of the analyte signals of the various measurements are compared and each time falling and rising peak heights of a particular drift time are ascertained with respect to the peaks of the measurement with smaller $\Delta t_{Rn}$ relative to the peaks of the measurements with larger $\Delta t_{Rn}$, the peaks of a particular shorter drift time with falling peak height are classified as the analyte signal of a monomer analyte ion and the peaks rising in intensity of a particular longer drift time are classified as a dimer analyte ion.

2. The method according to claim 1, wherein the difference in drift time between monomer analyte ion and drift time dimer analyte ion is used for identification of the analyte ions.

3. The method according to claim 1, wherein for the first measurement (n=1) the residence time $\Delta t_{R1}$ is within the measuring accuracy 0 and for the further measurements (n=2, 3, 4 etc.) the residence time $\Delta t_{Rn} = (n-1) \times 0.1$ to $0.5$ ms.

4. The method according to claim 1, wherein the pulse width $\Delta t_e$ of the ionization pulse I is not varied for the measurements.

5. The method according to claim 1, wherein the pulse width $\Delta t_F$ of the ion extraction pulse F is not varied for the measurements.

6. The method according to claim 1, wherein the time interval $\Delta t_e$ of the ionization pulse is between 0.1 microseconds and 10 milliseconds.

7. The method according to claim 1, wherein the time interval $\Delta t_F$ of the extraction pulse F is between 0.5 microseconds and 20 milliseconds.

8. The method according to claim 1, wherein the residence time $\Delta t_R$, i.e., being the time between one ionization pulse I and a following ion extraction pulse F, is between 10 microseconds and 100 milliseconds.

9. The method according to claim 1, wherein a tracer with known drift time is introduced into the reaction space to form dimer analytes.

10. The method according to claim 9, wherein a drift gas is passed through the reaction space.

11. The method according to claim 9, wherein the tracer is chosen from the group of organic compounds having at least one alcohol group (—OH) organic compounds having at least one keto group (C=O) or both.

12. The method of claim 9, wherein the drift gas is introduced together with a tracer into the reaction space in a constant concentration.

13. The method according to claim 9, wherein the proton affinity of the tracer and that of the analyte differs by not more than 100 kJ / mol.

14. The method according to claim 1, wherein the ionization process is carried out in the reaction space with a pulsed electron source.

15. The method according to claim 1, wherein the pulse width $\Delta t_e$ of the ionization pulse I is shorter than the pulse width $\Delta t_F$ of the ion extraction pulse F.

16. The method according to claim 1, wherein the time interval $\Delta t_e$ of the ionization pulse is between 1 microsecond and 1 millisecond.

17. The method according to claim 1, wherein the time interval $\Delta t_e$ of the ionization pulse is between 10 microseconds and 0.1 milliseconds.

18. The method according to claim 1, wherein the time interval $\Delta t_F$ of the extraction pulse F is between 5 microseconds and 2 milliseconds.

19. The method according to claim 1, wherein the time interval $\Delta t_F$ of the extraction pulse F is between 50 microseconds and 200 microseconds.

20. The method according to claim 1, wherein the residence time $\Delta t_R$ between one ionization pulse I and a following ion extraction pulse F is between 100 microseconds and 10 milliseconds.

21. The method according to claim 1, wherein a tracer with known drift time is introduced into the reaction space to form dimer analytes, and wherein the proton affinity of the tracer and that of the analyte differs by not more than 50 kJ / mol.

22. The method according to claim 1, wherein the difference in drift time between monomer analyte ion and drift time dimer analyte ion is used for identification of the analyte ions, by using a database of drift time differences for monomer/dimer analyte ions.

23. The method according to claim 1, wherein for the first measurement (n=1) the residence time $\Delta t_{R1}$ is within the measuring accuracy 0 and for the further measurements (n=2, 3, 4 etc.) the residence time $\Delta t_{Rn\ =(n-}1) \times 0.1$ to 5 ms, and the difference between each $\Delta t_{Rn}$ and $\Delta t_{Rn+1}$ is substantially constant.

* * * * *

UNITED STATES PATENT AND TRADEMARK OFFICE
CERTIFICATE OF CORRECTION

PATENT NO. : 8,604,422 B2  
APPLICATION NO. : 13/720259  
DATED : December 10, 2013  
INVENTOR(S) : Wolfgang Bäther and Frank Gunzer Page 1 of 1

It is certified that error appears in the above-identified patent and that said Letters Patent is hereby corrected as shown below:

On the title page of the Patent after item (71) Applicants:, delete "Wolfgang Bather, Lubeck" and insert -- Wolfgang Bäther, Lübeck --.

On the title page of the Patent after item (72) Inventors:, delete "Wolfgang Bather, Lubeck" and insert -- Wolfgang Bäther, Lübeck --.

On the title page of the Patent after item (73) Assignee:, delete "Dragerwork AG & Co. KGaA, Lubeck" and insert -- Drägerwerk AG & Co. KGaA, Lübeck --.

In the Claims

In column 8, on line 24, delete "time $\Delta t_R$, i.e., being the time between one ionization pulse I" and insert -- time $\Delta t_R$ being the time between one ionization pulse I --.

Signed and Sealed this  
Twenty-seventh Day of May, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,604,422 B2  
APPLICATION NO. : 13/720259  
DATED : December 10, 2013  
INVENTOR(S) : Wolfgang Bäther and Frank Gunzer Page 1 of 1

It is certified that error appears in the above-identified patent and that said Letters Patent is hereby corrected as shown below:

On the title page of the Patent, item (12), delete "Bather" and insert -- Bäther --.

On the title page of the Patent after item (71) Applicants:, delete "Wolfgang Bather, Lubeck" and insert -- Wolfgang Bäther, Lübeck --.

On the title page of the Patent after item (72) Inventors:, delete "Wolfgang Bather, Lubeck" and insert -- Wolfgang Bäther, Lübeck --.

On the title page of the Patent after item (73) Assignee:, delete "Dragerwork AG & Co. KGaA, Lubeck" and insert -- Drägerwerk AG & Co. KGaA, Lübeck --.

In the Claims

In column 8, on line 24, delete "time $\Delta t_R$, i.e., being the time between one ionization pulse I" and insert -- time $\Delta t_R$ being the time between one ionization pulse I --.

This certificate supersedes the Certificate of Correction issued May 27, 2014.

Signed and Sealed this  
First Day of July, 2014

Michelle K. Lee  
*Deputy Director of the United States Patent and Trademark Office*